United States Patent
Pether et al.

(10) Patent No.: US 9,973,611 B2
(45) Date of Patent: May 15, 2018

(54) DEVICE AND METHOD FOR SELF-ADMINISTRATION OF MEDICINE

(71) Applicant: One World Design & Manufacturing Group LTD, Warren, NJ (US)

(72) Inventors: Fred Pether, New Hope, PA (US); Matthew Coe, Annandale, NJ (US); Richard Costa, Bedminster, NJ (US)

(*) Notice: Subject to any disclaimer, the term of this patent is extended or adjusted under 35 U.S.C. 154(b) by 284 days.

(21) Appl. No.: 14/738,247

(22) Filed: Jun. 12, 2015

(65) Prior Publication Data
US 2016/0058661 A1    Mar. 3, 2016

Related U.S. Application Data

(60) Provisional application No. 62/044,005, filed on Aug. 29, 2014.

(51) Int. Cl.
| | |
|---|---|
| *H04B 1/38* | (2015.01) |
| *H04M 1/725* | (2006.01) |
| *A61J 7/00* | (2006.01) |
| *A61J 7/04* | (2006.01) |
| *G06F 19/00* | (2018.01) |

(52) U.S. Cl.
CPC ....... *H04M 1/72533* (2013.01); *A61J 7/0084* (2013.01); *A61J 7/0418* (2015.05); *A61J 7/0454* (2015.05); *A61J 7/0481* (2013.01); *G06F 19/3462* (2013.01); *A61J 2200/30* (2013.01); *A61J 2200/72* (2013.01)

(58) Field of Classification Search
None
See application file for complete search history.

(56) References Cited

U.S. PATENT DOCUMENTS

| | | | |
|---|---|---|---|
| 2006/0163977 A1* | 7/2006 | Meek, Jr. | E05B 47/0002 312/218 |
| 2013/0030566 A1* | 1/2013 | Shavelsky | A61J 7/04 700/244 |
| 2014/0055267 A1* | 2/2014 | Rothschild | A61J 7/0084 340/573.1 |
| 2014/0058560 A1* | 2/2014 | Kanagala | G06F 19/3462 700/240 |
| 2015/0196445 A1* | 7/2015 | Larkner | G06Q 10/087 312/209 |
| 2015/0378520 A1* | 12/2015 | Chandrasekaran | G06F 3/0482 715/716 |
| 2017/0140594 A1* | 5/2017 | Zastrow | G07C 9/00309 |

* cited by examiner

*Primary Examiner* — Jinsong Hu
*Assistant Examiner* — Alexander Yi
(74) *Attorney, Agent, or Firm* — Mitchell J. Mehlman, Esq.

(57) ABSTRACT

Devices and methods for improving user compliance with a pre-determined medication schedule including integrated software and hardware elements using wireless communication protocols to provide assistance to individuals who need to remember to administer one or more medications are provided.

5 Claims, 17 Drawing Sheets

REMINDER SCREEN WHEN CONNECTED TO MedQuaters

MEDICINE SCHEDULE SCREEN.

ADHERENCE TRACKING

DEVICE AND METHOD FOR SELF-ADMINISTRATION OF MEDICINE

CROSS-REFERENCE TO RELATED APPLICATION

This application claims priority of U.S. Provisional Patent Application Ser. No. 62/044,005, titled "An electronic device to help patients correctly self-administer injectable pharmaceuticals", filed Aug. 29, 2014, the disclosure of which is incorporated herein by reference in its entirety.

BACKGROUND OF THE INVENTION

Many pharmaceuticals and other medications are administered by injection. Increasingly, patients are injecting themselves as opposed to having to go to a doctor or hospital. Compared to swallowing a pill, injections can be complicated and uncomfortable. Patients are often confused about how to inject themselves and when to inject themselves. In some cases, it may be necessary for a clinical nurse educator to visit patients at their homes to help patients with injections, thus increasing the cost of treatment.

Known devices are focused on providing safe storage conditions for injectable materials. Other devices may include devices that function as sophisticated alarm clocks. There is a need for systems, devices, and methods that can enable a remote monitoring of patient compliance, such as the administration of an injection in the patient's home.

People often take one or more injectable medications several times a day to maintain or improve their health. Often, these medications or supplements must be taken at specific times each day. If medications or supplements are not taken at the proper times, individual health may be jeopardized. For example, failure to take a prescribed medication for treatment of diabetes can result in severe health consequences including death. Further, non-compliance with a prescribed regimen of one or more medications, particularly in the elderly and the aging population of "baby boomers", can result in billions of dollars of unnecessary health care costs.

Some people who take one or more medication a day are able to take medications without assistance. However, other people who take one or more medication or supplement a day require a reminder or the assistance of a care taker. Care takers may be one or more members of the patient's family or other individuals, such as friends, nurses, nurse's aids and the like. It can be difficult for a patient or a care taker to organize a patient's medications or supplements to insure compliance with a predetermined schedule. Further, it can be extremely difficult to monitor compliance with multiple medication schedules. Failure to properly monitor compliance can result in catastrophic health consequences to the patient and high levels of care taker anxiety, which can lead to increased health problems for care takers.

Known devices have severe limitations. One such limitation is the need to remind the patient to take their medication when the patient is away from the dispensing unit. Another such limitation is the inability for a user or a care taker to remotely monitor a patient's compliance with a medication schedule.

The present invention relates generally to devices and methods that include one or more sensors to time stamp the opening or closing of a storage box drawer or box lid utilized to store injectable or other medications. The devices can also include one or more sensors to record the temperature, such as the minimum and the maximum temperature, during storage or indicate the presence or absence of an individual dose, such as a syringe stored in a particular location. The devices can include one or more batteries and a wireless technology protocol, such as bluetooth or Wi-Fi, for exchanging data over distance from fixed units such a medicine storage containers and mobile devices, such as smart phones or computer tablets or other wireless personal area networks (PANs).

The present invention provides a communication channel between patients and healthcare providers, which will render home visits infrequent or unnecessary. The present invention solves these difficult problems in a novel manner.

Interactive medicine storage systems including multifunctional interactive wireless devices such as smart phone having programmable software that can communicate with one or more medicine storage box or dispenser and methods for monitoring and improving patient compliance using such systems are disclosed herein.

SUMMARY OF THE INVENTION

A medicine storage container can store injectable pharmaceuticals in a refrigerator or other environment. The storage box can open up a communication channel between patients and health care providers. In some embodiments, the container can be insulated.

In some embodiments, the container includes an external or internal temperature control system for maintaining an optimal temperature and preventing medicines stored in the container from becoming too warm or too cold.

In certain embodiments, a sensor can time stamp the opening or closing of a container lid or the opening and closing of a drawer.

In certain embodiments, a sensor can record the temperature or the maximum and minimum temperature inside the storage container.

Certain embodiments can include a battery and a wireless protocol antenna, such as a bluetooth device, that sends information to a smart phone or other wireless device. A storage box having a lid can be locked while in a refrigerator for reasons of child safety and patient privacy. The wireless antenna can be paired with the smart phone or other wireless device, thus disabling a lock and allowing the lid to open freely when the user requires medicine.

In some embodiments, the device can produce information that is useful to a patient, for example, the previous five injection sites can be displayed on a smart device. Location information can be important because the patient must typically rotate injection sites. Data for health care professionals, for example, how many self-injections were performed at the right time and how many were skipped can be provided to help monitor patient compliance.

In one non-limiting embodiment of the invention, an insulated container is designed to store injectable medicines. A sensor, such as a mechanical, electrical or optical sensor can interact with a hinged lid of the container. The sensor can also enable locking of the container when the container is not "paired" with a wireless signal, such a bluetooth protocol and a smart phone, tablet or other wireless device. The device can include a rechargeable battery or alternatively a replaceable battery.

In some embodiments, a light, such as for example, an LED light, can be used to signal the user that a dose is ready or that the system has malfunction.

In certain embodiments, a smart phone or computer tablet includes a preloaded application for command, control, data management and user interface functions.

In some embodiments, a temperature sensor can record the temperature in a storage container over time and can send temperature data via a wireless antenna to a smart phone application for user analysis or monitoring patient compliance.

In one embodiment manufacturing the battery has sufficient power to ensure that the sensors, and the wireless transmitter and receiver can send opening/closing data to a smart phone or tablet. One suitable type of plastic for manufacturing these devices is ABS. Another method of manufacturing a storage box can use nylon or card stock with each component being sewn or glued with insulation to form the structure of the container.

In some embodiment, an optional light, such as an LED light on the device can be utilized to show that the wireless communication system has successfully paired with the smart phone or other computer device by, for example, turning green instead of white. Additionally, a red light can indicate that the battery is low and may need recharging or replacing.

In some embodiments the device and be configured to achieve the desired goal, for example a sensor that records the opening and closing of the storage box could be used alone or in combination with a sensor on a disposal container to record when a user disposes of a syringe.

In some embodiments, storage box can be a free standing unit with built in refrigeration and can include its own power supply, thus making a separate refrigerator unnecessary when refrigeration is required. This embodiment can have great utility where the patient has a lifestyle that necessitates frequent travel.

In certain embodiments, device can produce information that is useful to a patient, for example, the previous five injection sites. This information is important information because the patient must typically rotate injection sites. The device and also provide useful information for health care professionals, for example, how many self-injections were performed, the time at which each injection was performed, or how many injections were missed.

In an apparatus according to one aspect of the invention, an apparatus for improving patient compliance can have a housing. The housing can include a lid and a lock for locking or unlocking the lid. A sensor can be configured to detect the position of the lid (e.g. open or closed). The sensor can be attached to the housing. A wireless transceiver for transmitting the position of the lid to a smart phone application can be attached to the housing. A smart phone can be capable of wirelessly commanding the lock to an open position or to a closed position. The smart phone can run the smart phone application for determining a pre-determined time for reminding a user to unlock the lid based on a medication data set input by the user and for receiving and recording the position of the lid.

In certain embodiments, the apparatus can include a manual by-pass switch for opening the lid in case of an emergency.

In certain embodiments, the apparatus can include a light for signaling the user that the lid is unlocked.

In some embodiments of the present aspect, the apparatus can include a light sensor for detecting when the apparatus is stored in a dark condition or a light condition, thereby commanding the apparatus to enter a sleep mode for saving power when the apparatus is in a dark condition or to enter an awake mode for wireless operation when the apparatus in a lighted condition.

In certain embodiments, the data set can comprise a name of at least one medication, a strength of at least one medication, and a schedule for taking at least one medication.

In some embodiments, the smart phone can communicate an alarm to the user according to the schedule.

In certain embodiments of the present invention, the wireless transceiver can communicate a signal to a user database. The signal can indicate at least one time when the lid has been opened and at least one time when the lid has been closed.

In other embodiments, the user database can store data indicating whether or not the lid has been opened and can allow at least one user to monitor a user compliance with the schedule for taking at least one medication.

In another aspect of the invention method of improving patient compliance with a pre-determined medication schedule can comprise the steps of entering a medication data set into a smart phone application; loading one or more medications into a lockable housing; receiving an alarm from the smart phone application; and using a wireless protocol to unlock the housing to access one or more medications.

In certain embodiments of this aspect the medication data set can include the name of one of more medication; the strength of one or more medication; and the time that one or more medication is to be taken.

In other embodiments, the method can further include the step of transmitting data to a secure server database. The data can include confirmation of a time when the housing was unlocked or the housing was locked.

In certain embodiments, the method can further include the step of transmitting an alarm when the lockable housing is not unlocked within a predetermined time from a scheduled dispensing time.

In another aspect of the invention, an apparatus for improving patient compliance can comprise a housing. The housing can have a drawer and a lock for locking or unlocking the drawer and the housing. A sensor can be configured to detect a position of the drawer. A wireless transceiver can transmit the position of the drawer to a smart phone application. A smart phone can be capable of wirelessly commanding the lock to an open position or a closed position. The smart phone can run the smart phone application for determining a pre-determined time to remind a user to unlock said drawer based on a medication data set input by the user and for receiving and recording the position of the drawer.

In one embodiment of this aspect, the apparatus can include a manual by-pass switch for opening the drawer.

Certain embodiments of this aspect can include a light for signaling the user that the drawer is unlocked.

In other embodiments, the apparatus can include a light sensor for detecting when the apparatus is stored in a dark condition or a light condition. The sensor can command the apparatus to enter a sleep mode for saving power when the apparatus is in a dark condition or to remain in an awake mode for operation when the apparatus is in a light condition.

In one embodiment of this aspect, the data set can include a name of at least one medication, a strength of at least one medication; and a schedule for taking at least one medication.

In a particular embodiment, the smart phone can communicate an alarm to the user according to the schedule.

In yet another aspect of the present invention, an apparatus for improving patient compliance can include a housing. The housing can have a drawer and a lock for locking or unlocking the drawer to the housing. A sensor can be configured to detect a position of the drawer. A wireless transceiver can be detachable from the housing. A smart phone can be capable of wirelessly commanding the lock to an open position or to a closed position. The smart phone can run the smart phone application for determining a predetermined time to remind a user to unlock the drawer based on a medication data set input by the user and for receiving and recording the position of the drawer.

In one embodiment of this aspect, the apparatus can include a light sensor for detecting when the apparatus is stored in a dark condition or in a light condition. Base on the sensor output signal, the apparatus can enter a sleep mode for saving power when the apparatus is in a dark condition or can remain in or enter into an awake mode for operation when the apparatus in a light condition.

DETAILED DESCRIPTION

Figure 1:
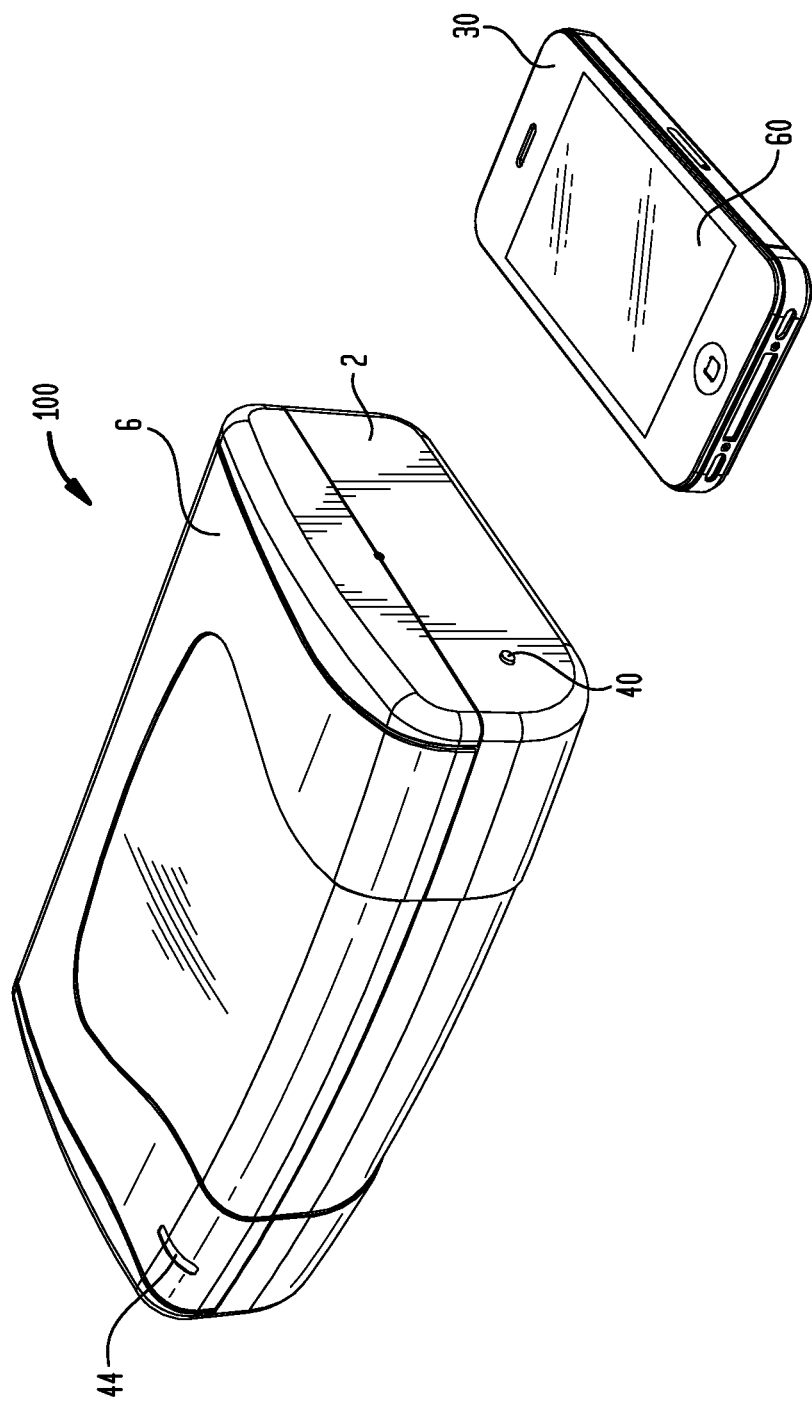
FIG. 1 depicts an isometric view of a device for self-administration of medicines according to one embodiment of the present invention.
Figure 2:
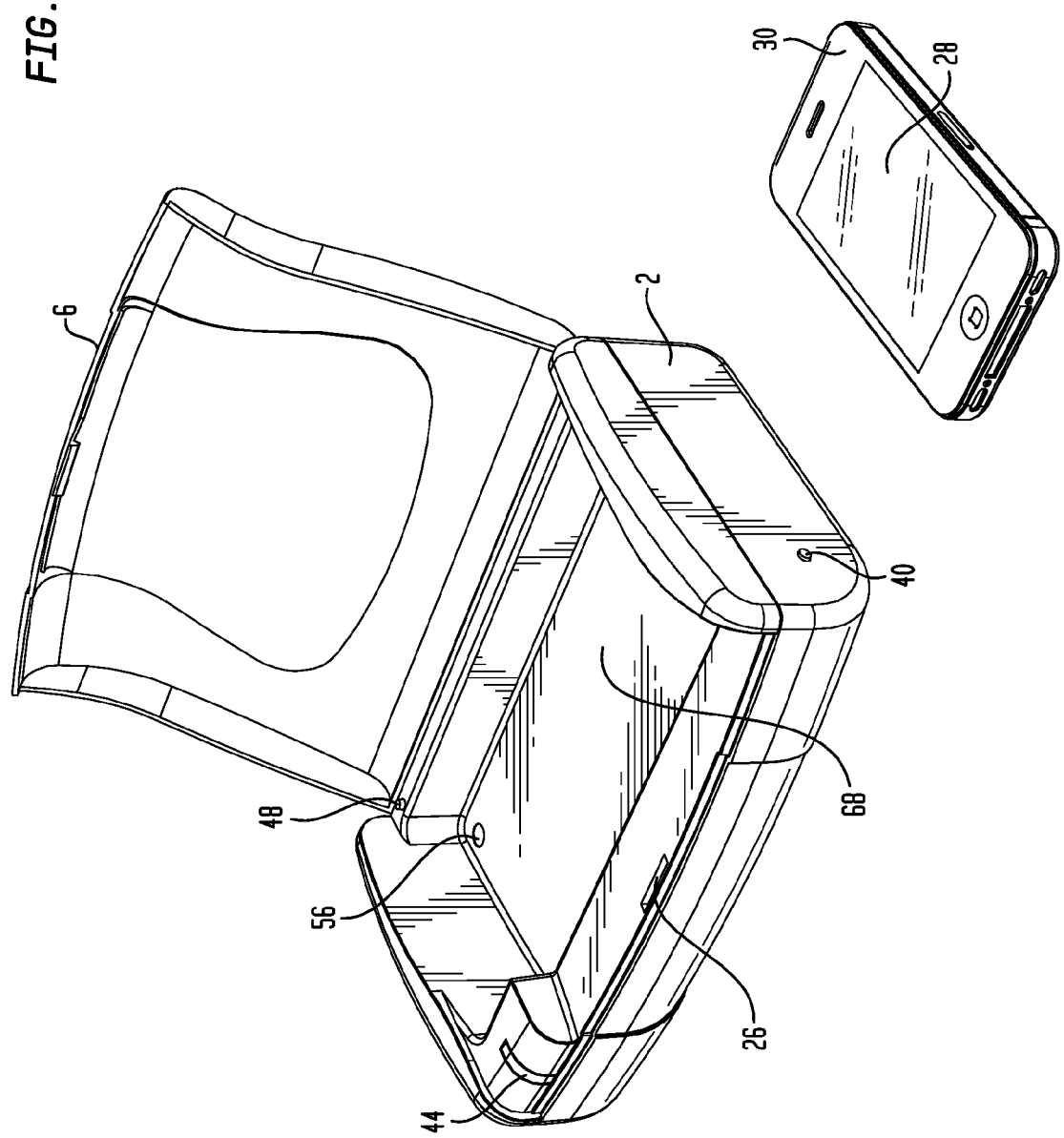
FIG. 2 is another isometric view of some of the elements included in the device of FIG. 1.
Figure 3:
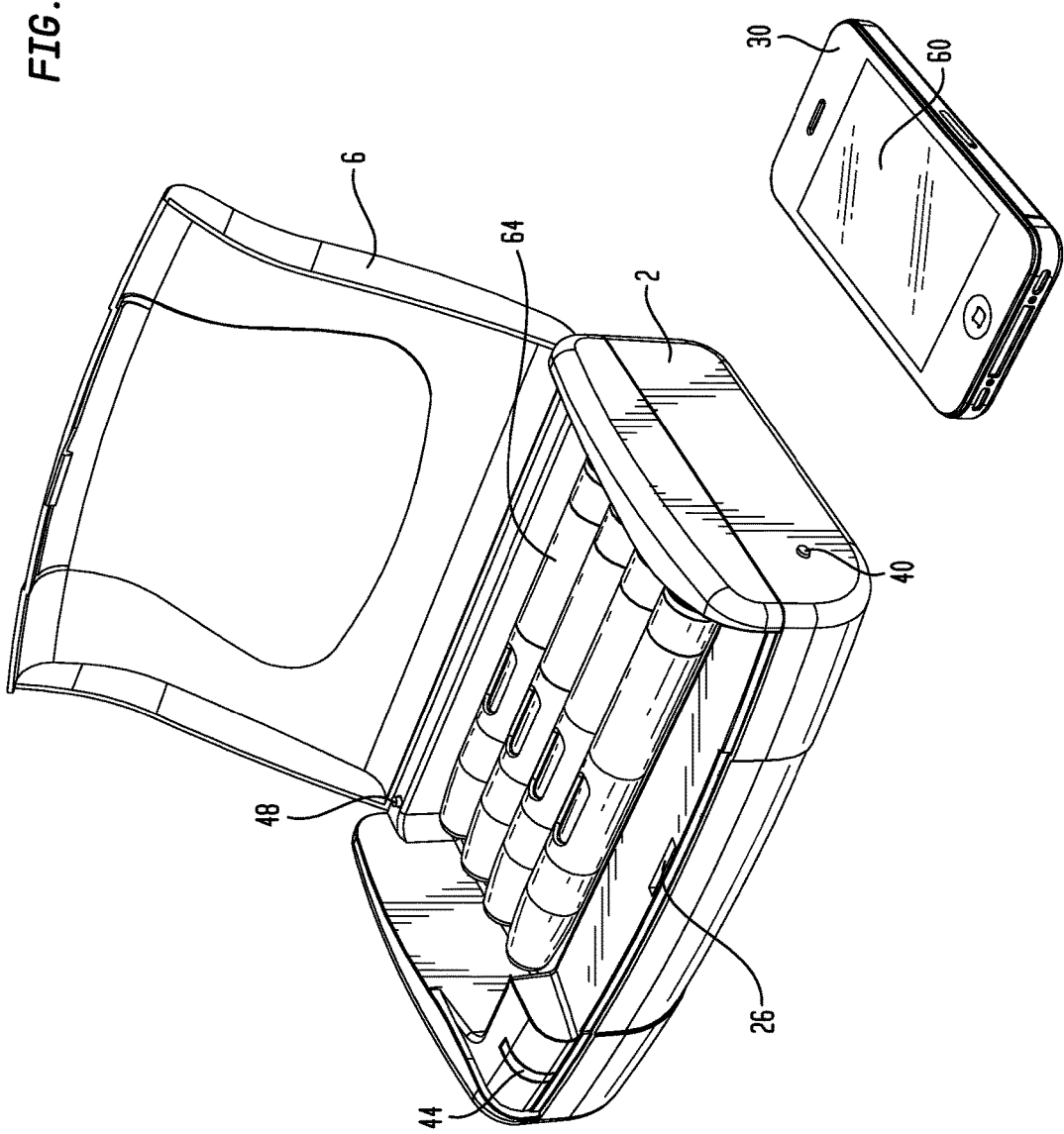
FIG. 3 is an isometric view of some of the elements included in the device of FIG. 1 depicting medicine injectors loaded in the device.
Figure 4:
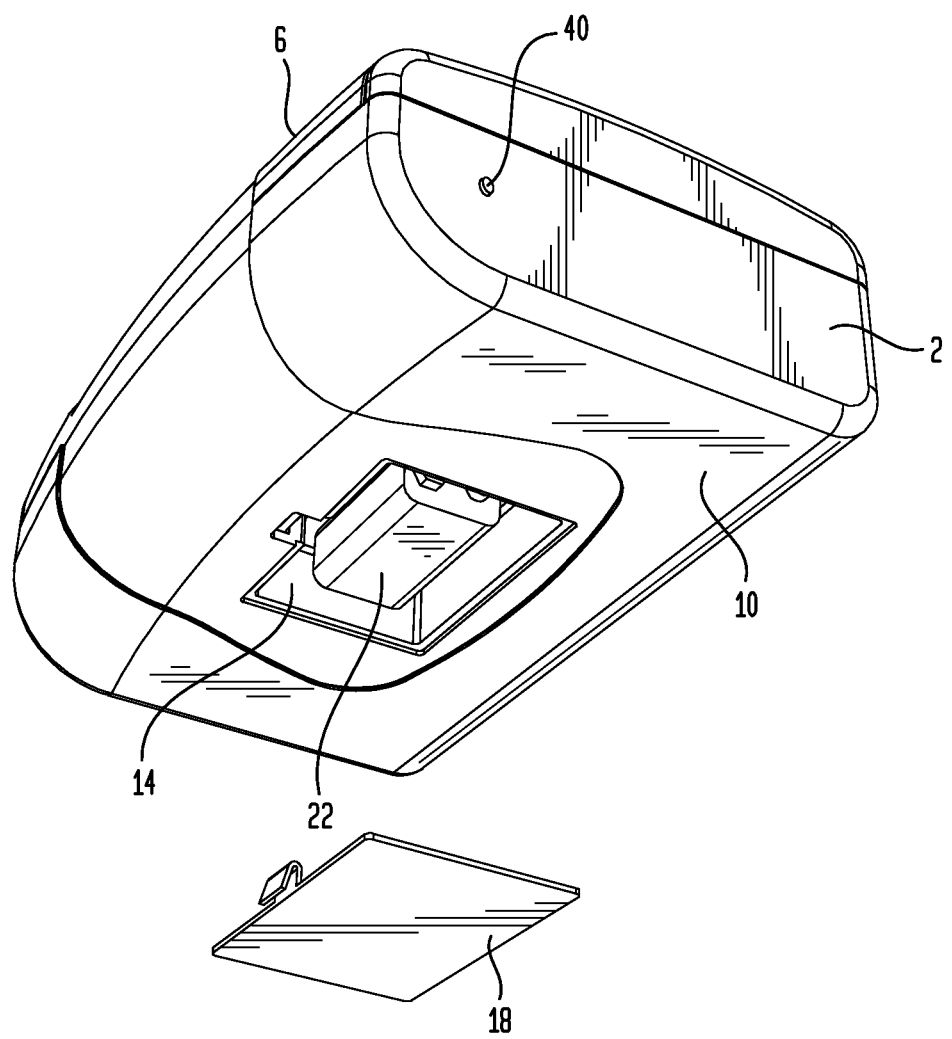
FIG. 4 is another isometric bottom view of some of the elements included in the device of FIG. 1.
Figure 5:
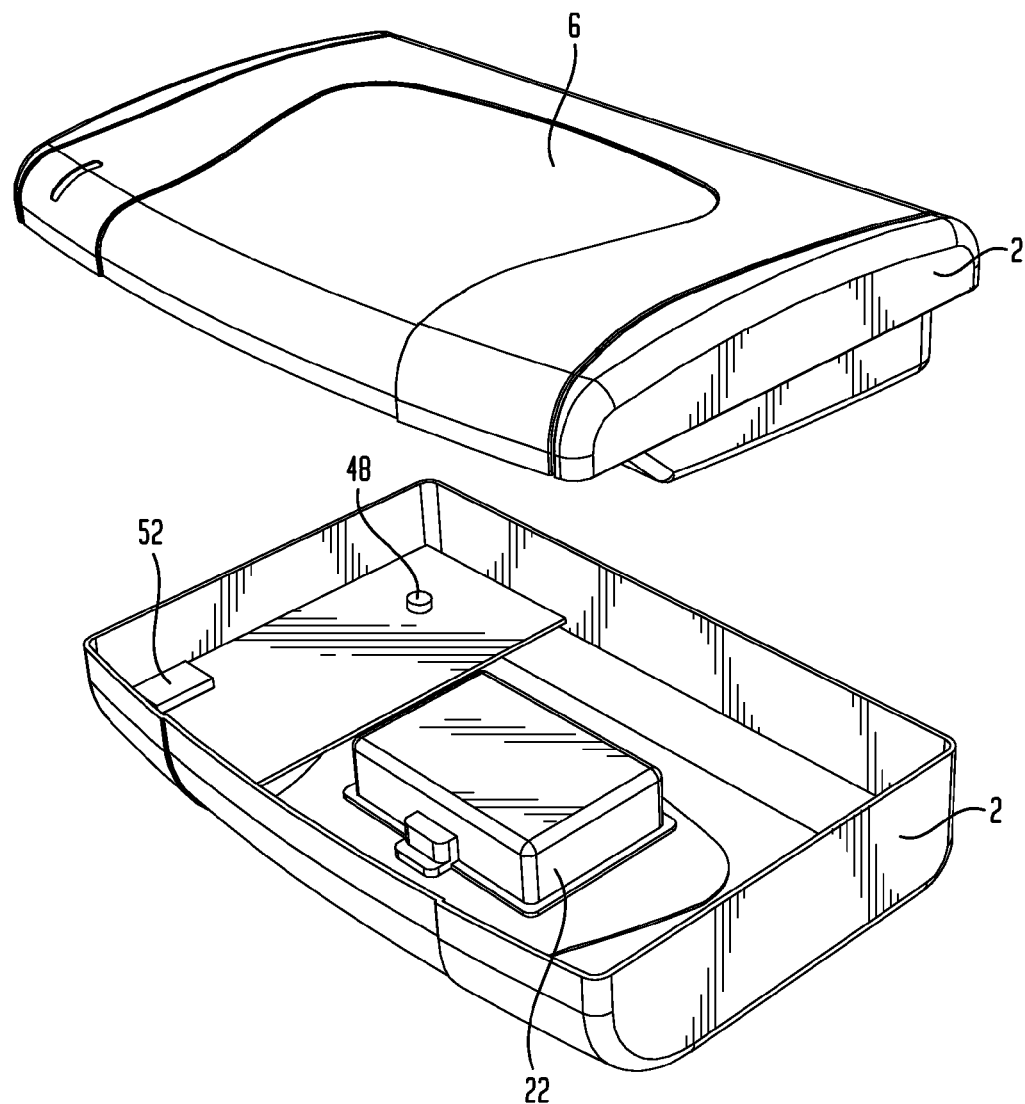
FIG. 5 is an exploded view of some of the elements included in the device of FIG. 1.

As used herein, the terms medicine and medicines refer to prescription and over-the-counter medications, dietary supplements such as vitamins, minerals or cosmetic products. Further, the terms medicine and medicines can refer to any product in an injectable form which the user has a need or desire to use on a predetermined, scheduled basis.

As used herein, the terms bluetooth, wireless, wireless communication or wireless protocol includes bluetooth, Wi-Fi and other known or future methods for secure wireless protocol that use electromagnetic radiation to connect wireless-enabled computers and devices to each other. Bluetooth simplifies communications between bluetooth-enabled computers and devices by creating personal area networks (PANs). To create a bluetooth PAN, a user must have at least two devices that contain bluetooth electronics. A person of ordinary skill in the art will understand that a variety of wireless command, control, and data systems can be used in the instant invention.

The operating range for a given device depends on the device class. One type is primarily used in computers and mobile devices, such as cell phones, PDAs, or MP3 players. The operating range is about 30 feet (10 meters). Not all wireless or bluetooth interfaces are the same. There are different versions of drivers with different interfaces as will be understood by a skilled artisan.

Bluetooth is only one standard wire-replacement communications protocol primarily designed for low-power consumption, with a short range based on low-cost transceiver microchips in each device. Because the devices use a radio (broadcast) communications system, they do not have to be in visual line of sight of each other, however a quasi-optical wireless path must be viable. A person of ordinary skill in the art of electronics will understand how to implement a wireless protocol such as blue tooth or Wi-Fi communication protocol between a storage container for injectable medicines and a smart phone or other wireless device designed to communicate with a medicine storage container.

As used herein the term "smart phone" or "smart device" includes any device capable of wireless command, control, and data management including but not limited to phones, tablets, lap-tops, computers, and other devices that can run software applications and utilize known or future wireless communication protocols to communicate with a remote device.

In one non-limiting embodiment of the present invention as shown in FIGS. 1-4, device 100 includes a housing 2 and a lid 6 being lockable to the housing to form a closed or an open unit. Bottom surface 10 of housing 2 includes an aperture 14 for a removable door 18 for accessing battery 22 located within the housing. The battery can be used to provide power to the device. Alternatively, a hardline power source can also be used.

The housing 2 includes an automated locking mechanism 26 to lock the lid of housing until a medication dose is scheduled to be taken. The locking mechanism is operated by a smart phone application 60 (See FIGS. 6-7) using a wireless communication protocol and a smart phone 30. When the pre-determined time set in the application occurs, and the smart phone 30 is in wireless proximity with a wireless electronic communication module 52 in the housing, the housing and the smart phone are "paired", thus enabling the lock to open and allow a user access to the medicine via by opening the lid. A signal from the smart phone via the blue tooth protocol will enable a mechanical device such as a solenoid, actuator or magnet to open or close the lock (not shown). A person of ordinary skill in the electro-mechanical arts will understand that the locking and unlocking function can be carried out in a number of known ways.

The housing can include by-pass switch 40 to allow a user to unlock the lid in case of emergency or malfunction and to allow access to the contents of the housing. The use of the by-pass switch can be electronically recorded and sent to the smart phone application for review and analysis.

The housing 2 can include a light 44, such as, for example an LED light, or an illuminated area which can illuminate, change color, or flash when it is time to take a medication stored inside the housing, when the device malfunctions, when the device is paired to a smart phone, or when the device is low on power.

In this embodiment, housing 2 includes switch 48 for sensing when the lid is opened or closed. The switch 48 can be, for example, an electrical switch, a mechanical switch, or an optical switch or other sensor. The housing 2 also includes a wireless transceiver or chip set 52 and associated hardware necessary to carry out the wireless command and control function and to communicate information to the smart phone and the application 60 residing on the phone. Information regarding the status of the lid, including when it is opened and closed, or how many times it opened or closed, can be transmitted to the smart phone and utilized by the application to provide user data.

In this embodiment, temperature sensor 56 can be used to track the temperature of the housing where medicine resides in order to monitor the condition of the medicine. The sensor 56 can send temperature data via the wireless connection protocol to the smart phone which can be utilized by the application to provide user data about temperature conditions during storage, such as, for example, the minimum and maximum temperatures over time.

In use, a user installs custom software application 60 on smart phone 30. After the application "pairs" the smart phone with wireless chip set or wireless transceiver 52 in the housing, the lock 26 can be disengaged and the user can open the lid 2.

Next, the user can load injectable materials 64 or other medicines into the storage area of the housing and close the lid to lock the contents inside the housing and start a dosing regimen.

In this embodiment, the application can be programmed to send the user an alarm on the smart phone or illuminate the light 44 on the housing at pre-determined times.

When the user next approaches the device, (i.e. the smart phone and device will remain "paired" and will connect wirelessly when the phone is in range of the housing) the smart phone application can be used to open the locking mechanism by sending a wireless signal to actuate the locking mechanism. The user can now access the medicine 64 stored in the device.

When the user accesses the medicine, the sensor can electronically time stamp each time the lid is opened or closed. This data can be sent to the smart phone application for review and analysis. After each use, the lid is closed and locked. A timer in the application restarted so that when the next dose is due, the process is repeated.

Figure 6B:
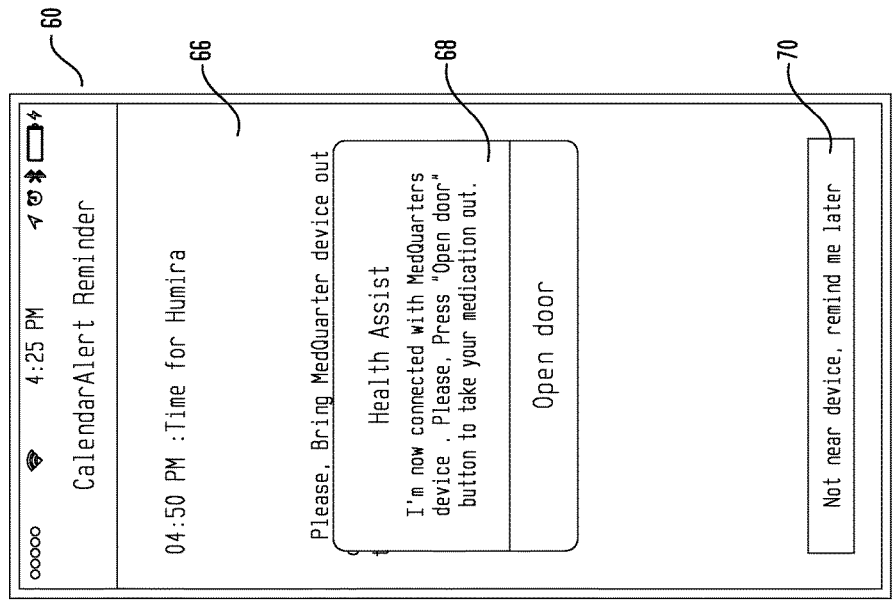
FIG. 6B depicts a reminder screen on a smart phone application according to various embodiments of the invention.
Figure 6A:
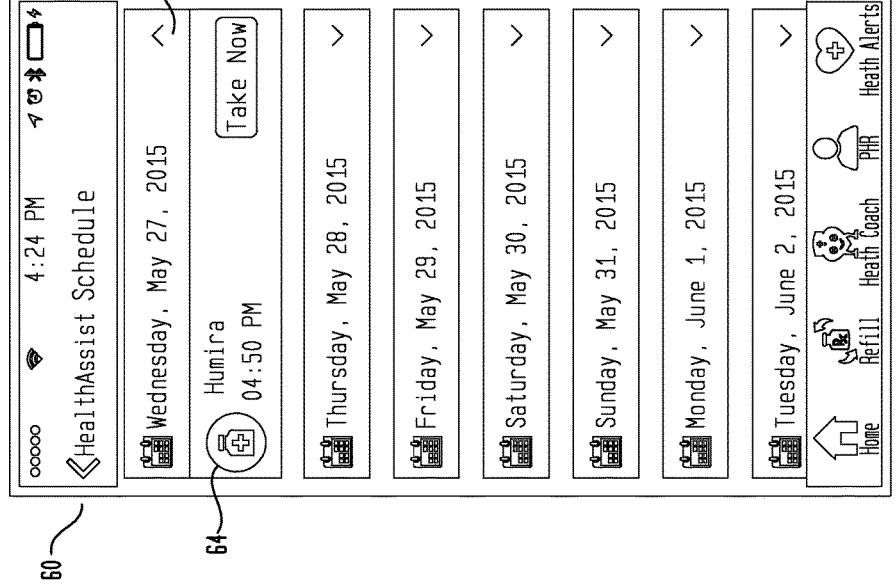
FIG. 6A depicts a medicine schedule screen on a smart phone application according to various embodiments of the invention.

Referring to FIGS. 6A and 6B, in one embodiment, the smart phone application 60 includes a scheduling screen 62. When a medicine is due, the use will receive a visual or audible prompt 64. As the user approaches the device 100 with the paired smartphone, the application can display a reminder screen 66 (FIG. 6B) in order to prompt the user to open the lid 68 or to snooze until a later time when the user wants to take the medicine.

Figure 7B:
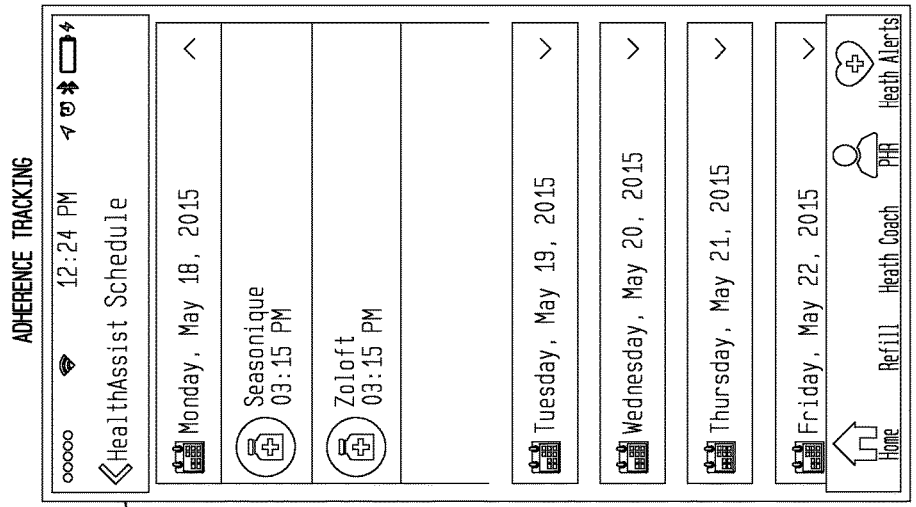
FIGS. 7A, 7B, and 7C depict three different screens on a smart phone application for tracking and displaying patient compliance data according to various embodiments of the present invention.
Figure 7A:
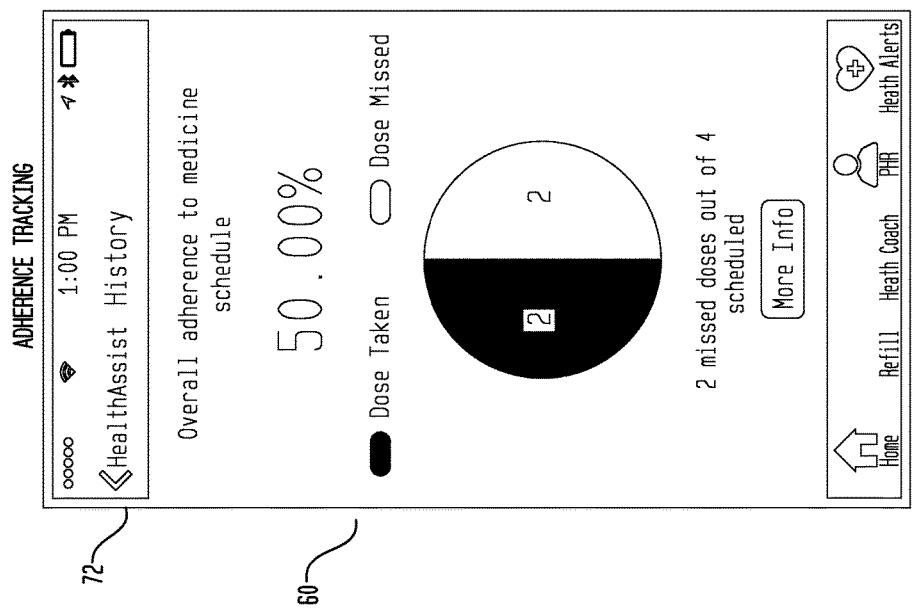
Figure 7C:
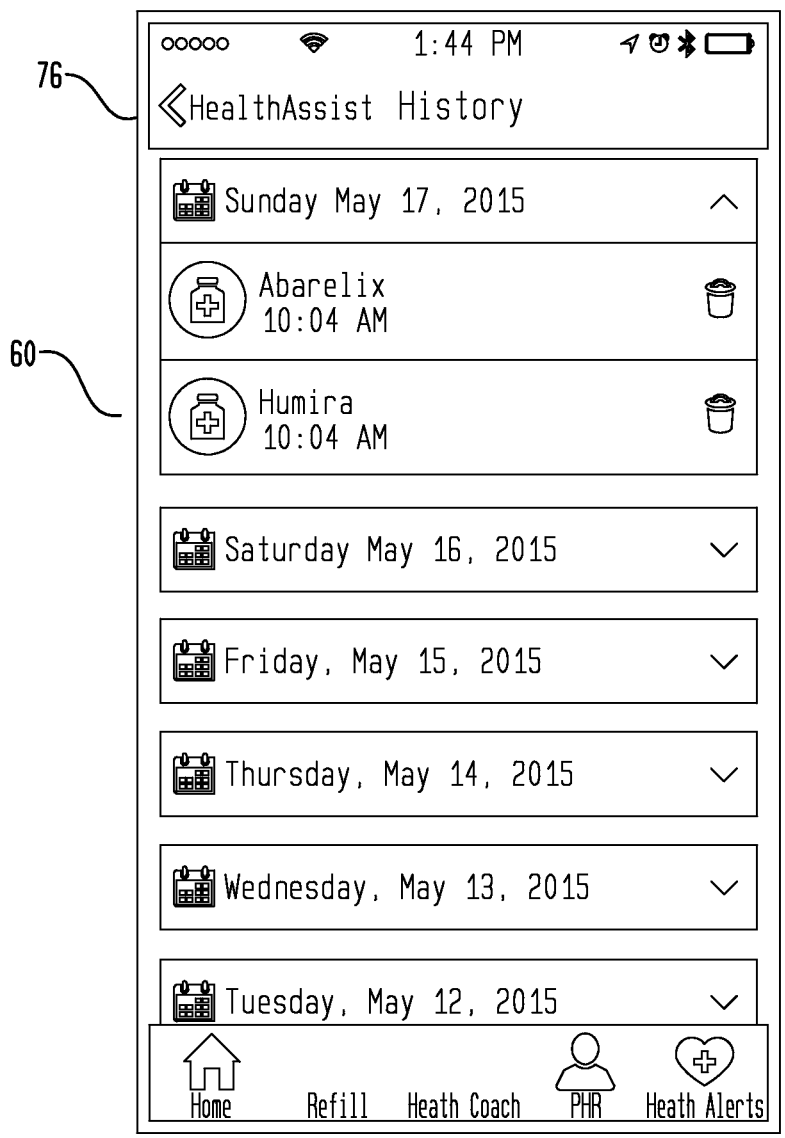
Figure 8:
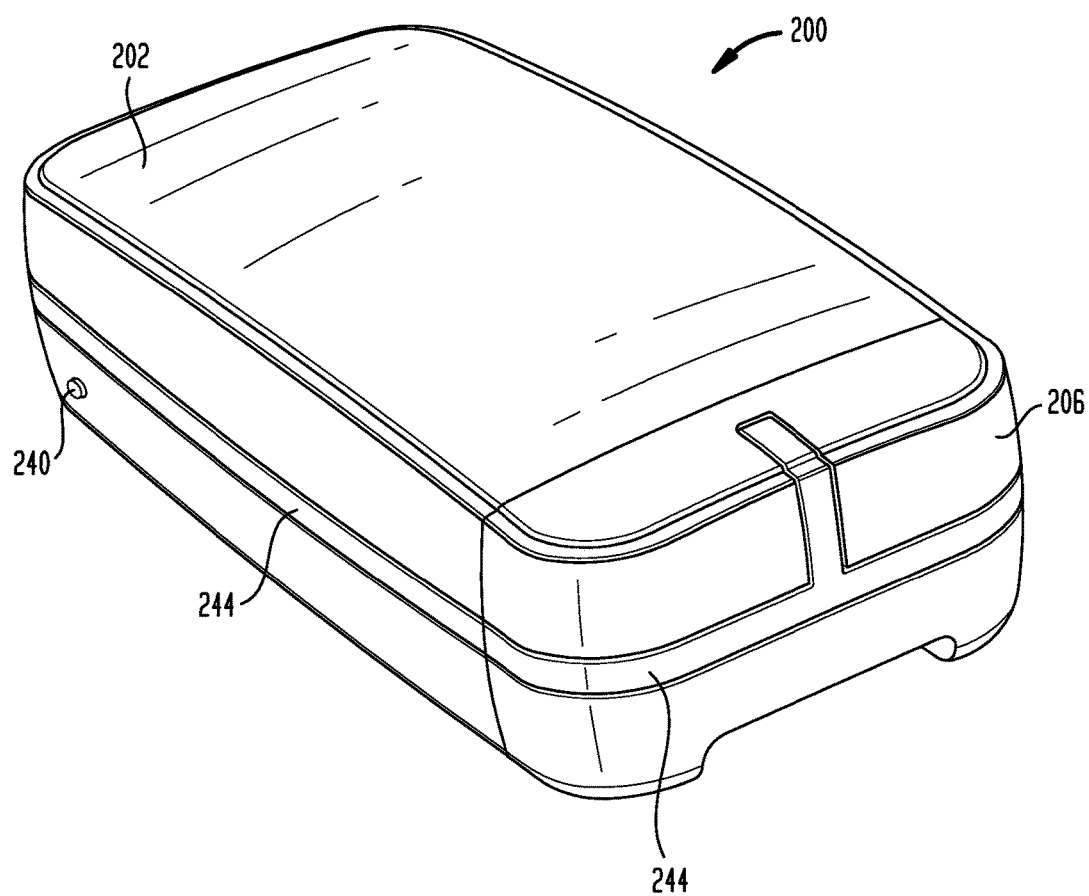
FIG. 8 depicts an isometric view of a device for self-administration of medicines according to one embodiment of the present invention.
Figure 9:
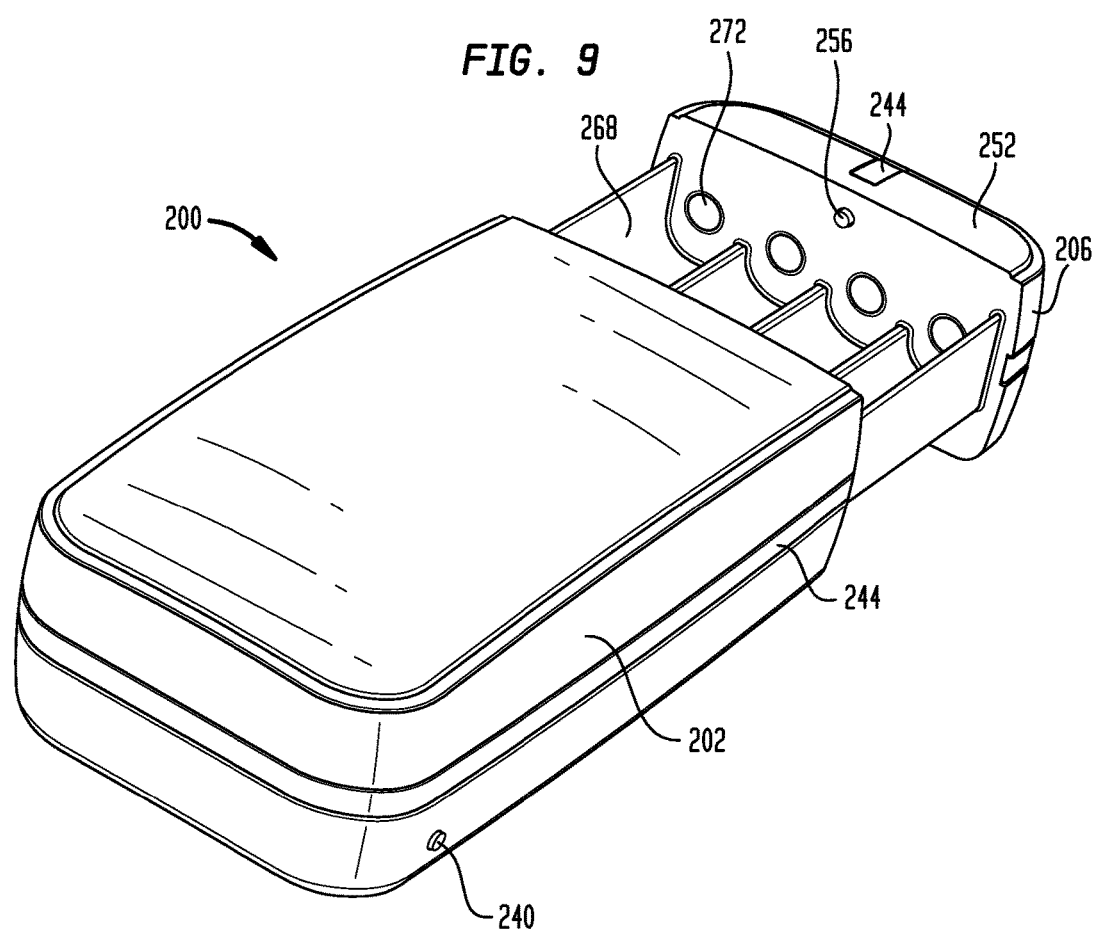
FIG. 9 is an isometric view of some of the elements included in the device of FIG. 8 showing a drawer in an open configuration.
Figure 10:
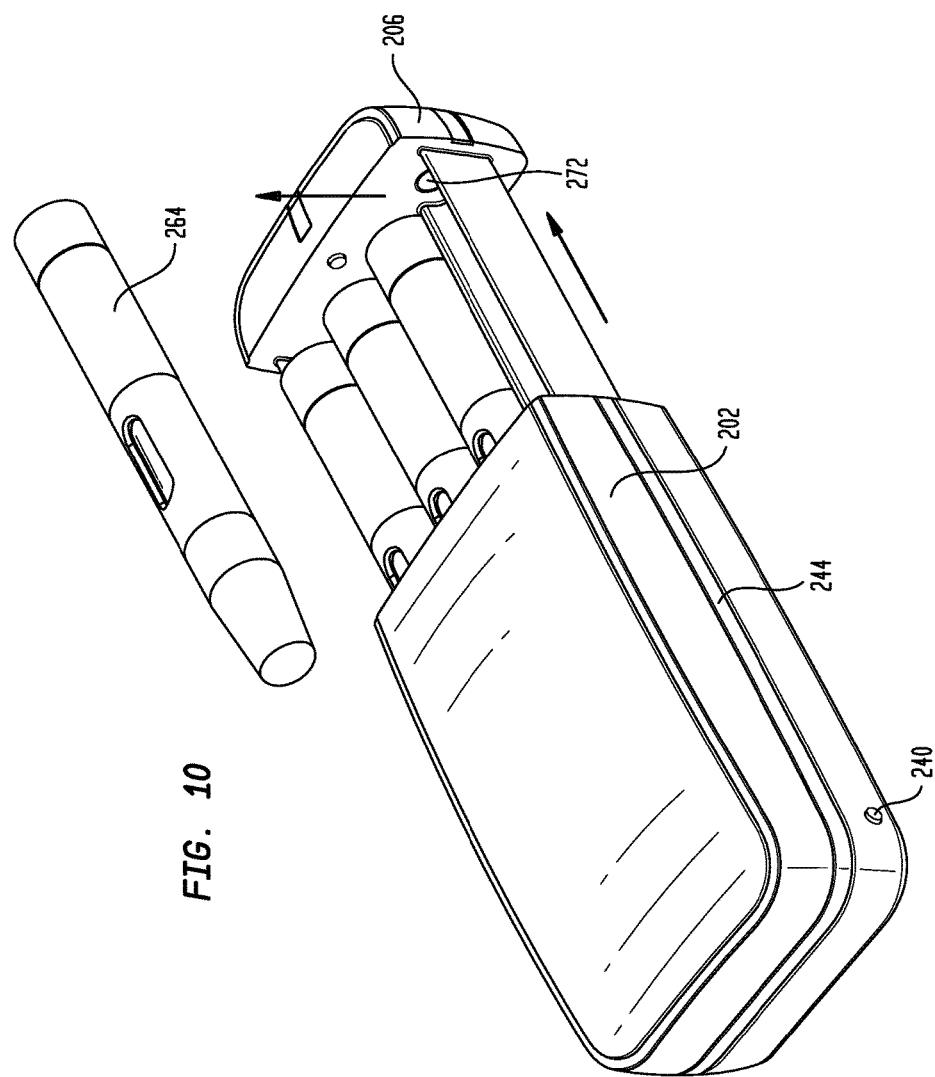
FIG. 10 is an isometric view of some of the elements included in the device of FIG. 8 showing a drawer in an open configuration and several medicines loaded in the draw in proximity to sensors.
Figure 11:
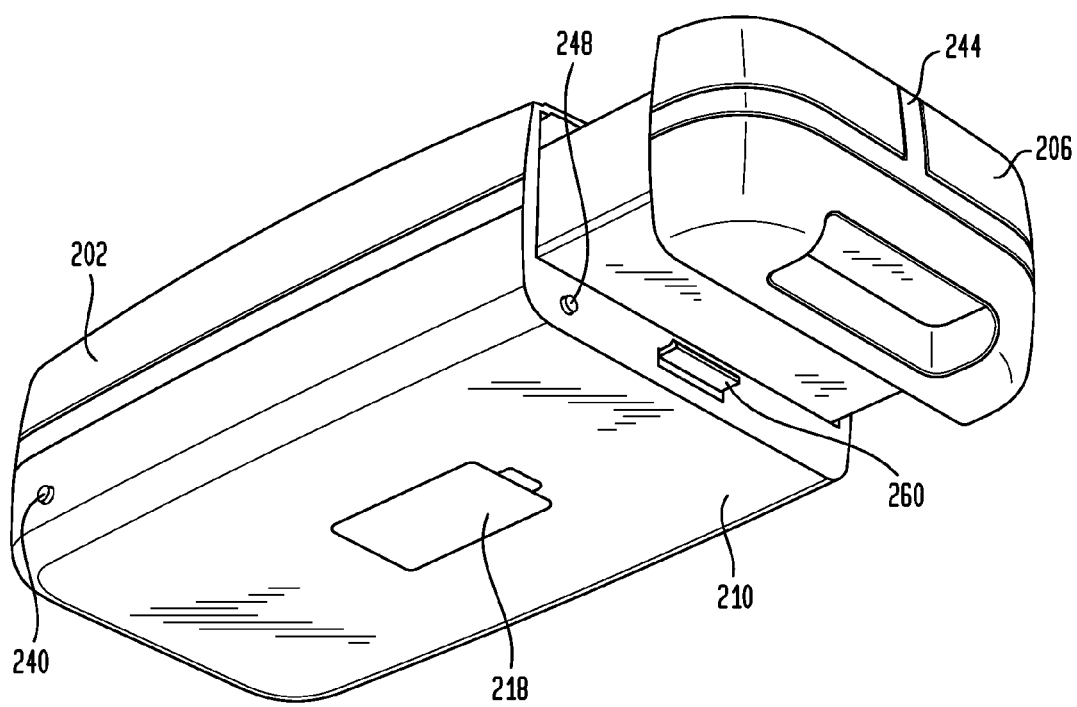
FIG. 11 is an isometric view of some of the elements included in the device of FIG. 8.
Figure 12:
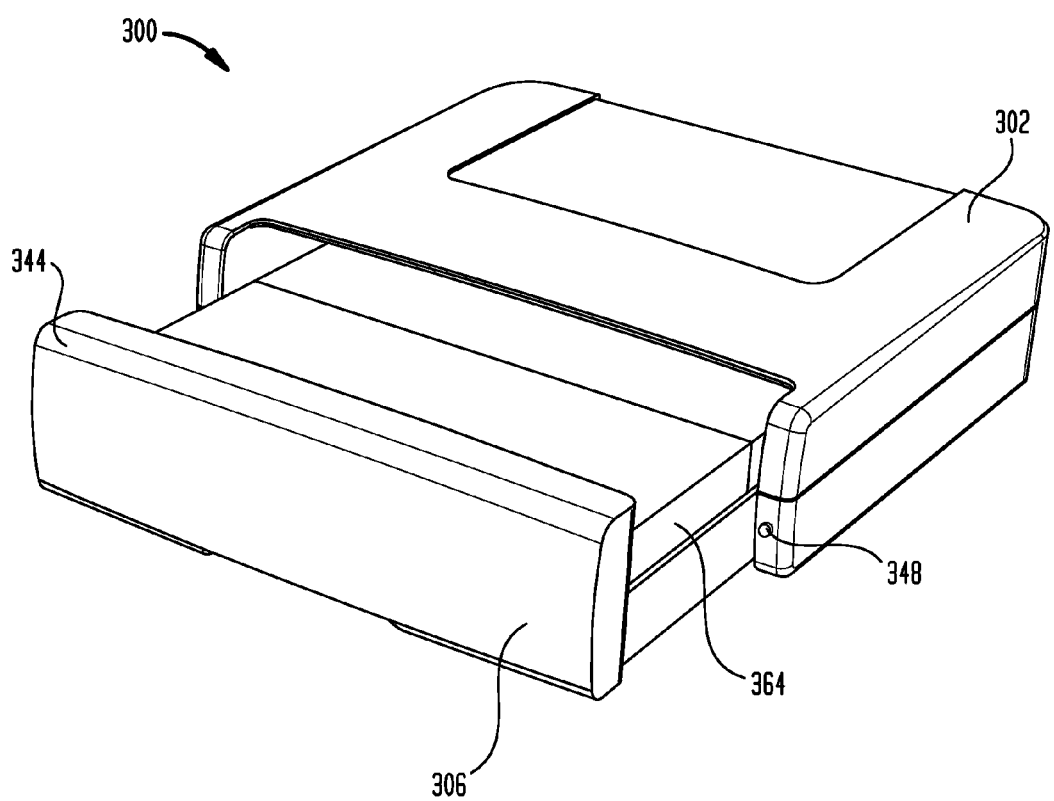
FIG. 12 depicts an isometric view of another embodiment of the present invention.
Figure 13:
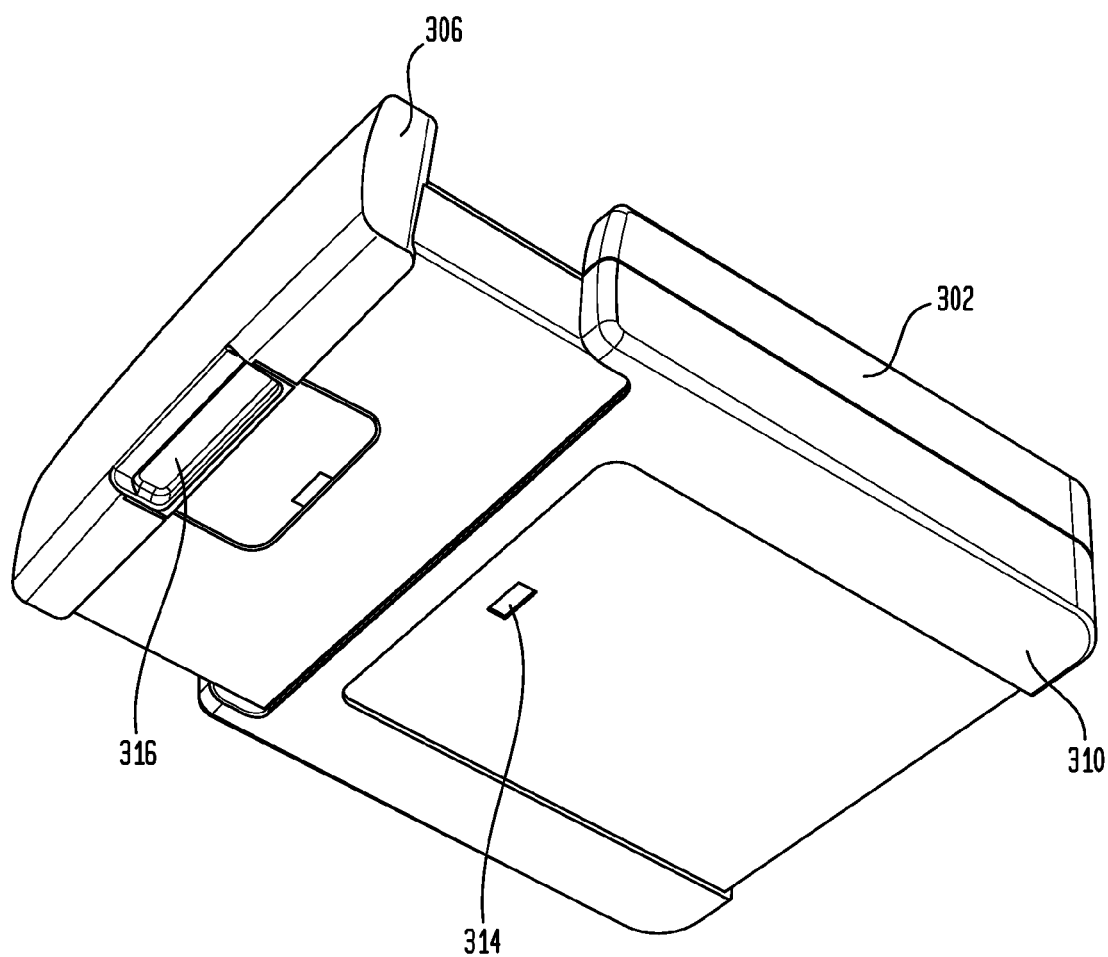
FIG. 13 shows another isometric view of the embodiment shown in FIG. 12.
Figure 14:
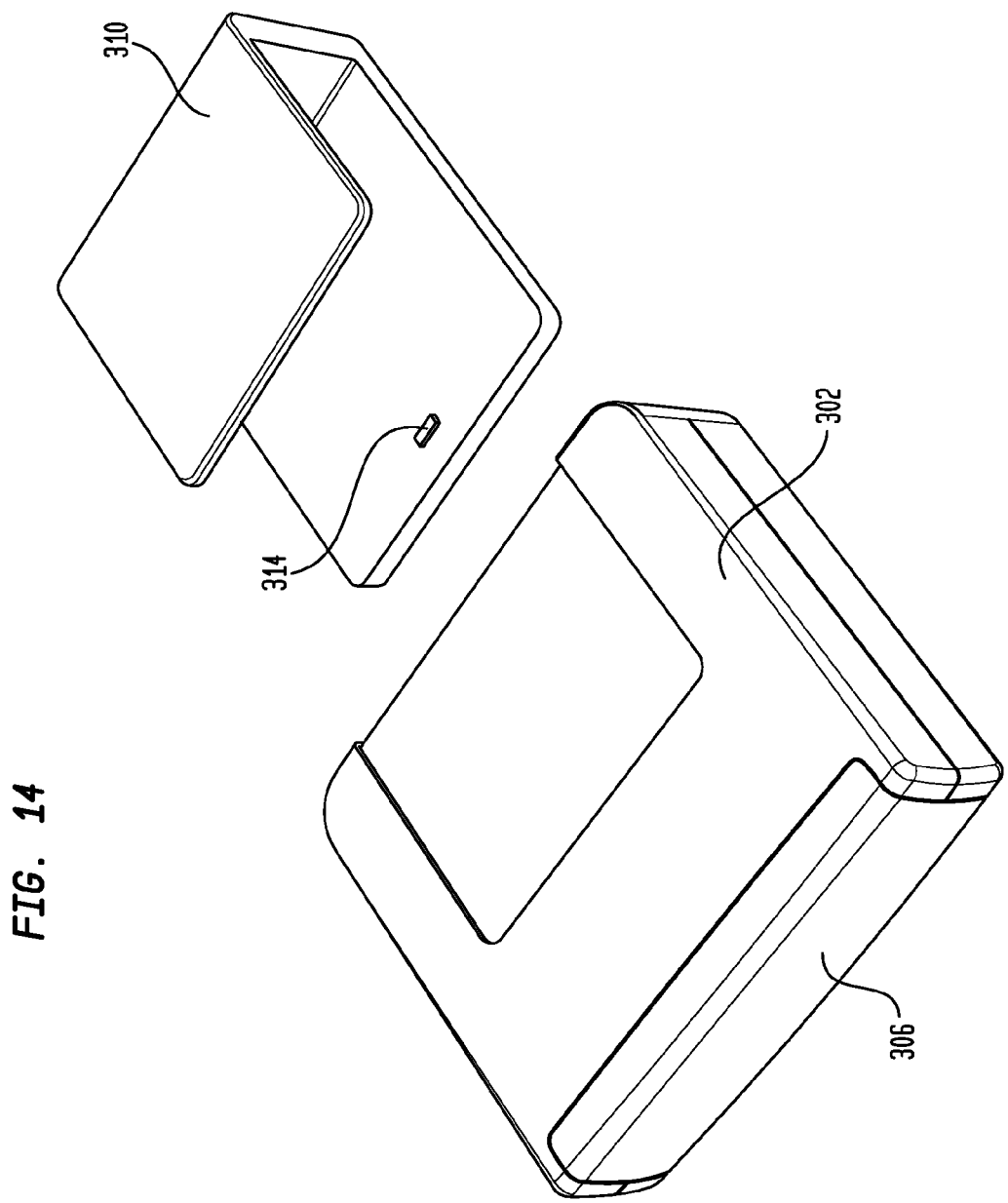
FIG. 14 is another isometric view of some of the elements of the embodiment shown in FIG. 12 including a smart wireless element.
Figure 15:
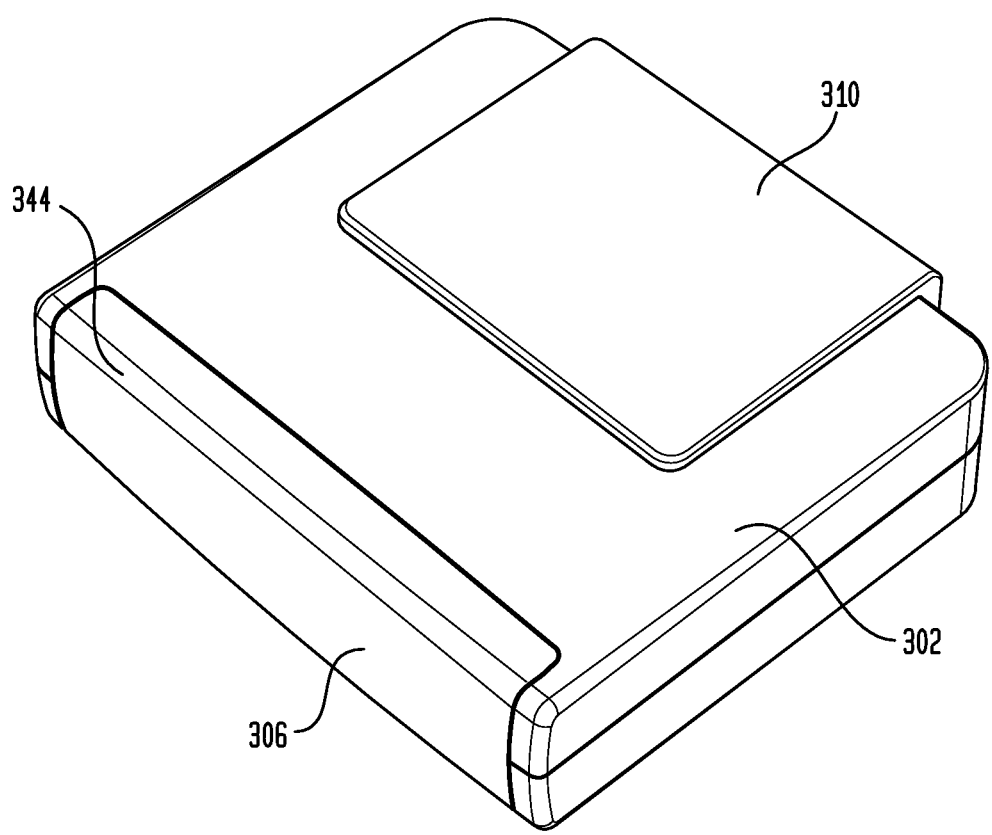
FIG. 15 is an isometric view of smart wireless element shown in FIG. 14 in an installed position.
Figure 16:
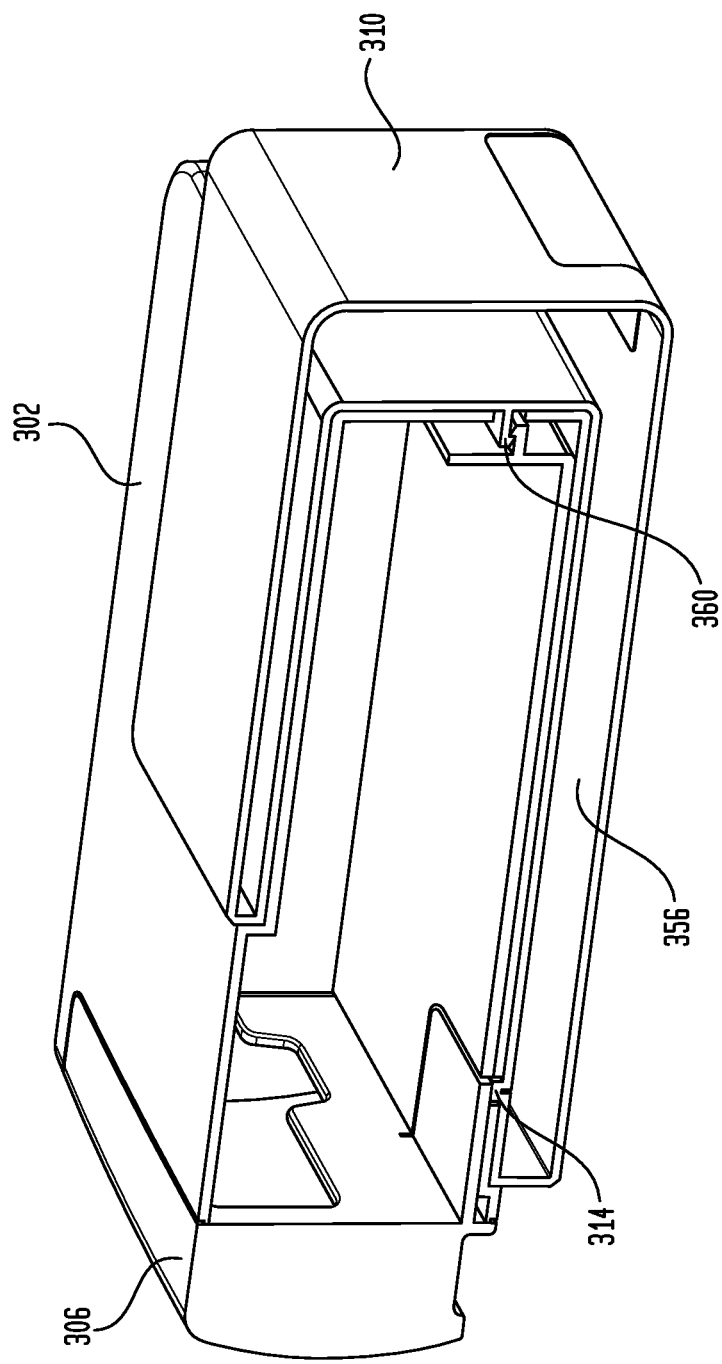
FIG. 16 is a cross-sectional view of some of the elements of the embodiment shown in FIG. 12.

Referring to FIGS. 7A-7C, three example screens of application 60 are shown. Screen 72 depicts an adherence chart indicating the overall patient compliance to the medicine schedule. Screen 74 depicts a schedule screen that shows the user which medicines are due, the time and the date due. Screen 76 depicts the history of when the medicine was taken so that a user may review the prior dosing history.

In some embodiments, the housing includes a battery or a rechargeable battery. Optionally, the housing can be powered by an external power source, such as by a plug and power outlet and can include a backup battery in case of power failure.

In one embodiment, the housing can include a light sensor to determine whether the housing is in a lighted place or in a dark place. If, for example, if the housing is kept in a dark refrigerator, the sensor can signal the device to enter a "sleep mode" thereby saving power and extending the life of the battery. When the refrigerator is opened and ambient light is detected by the sensor, the device will enter a "wake" mode to perform its required functions as discussed above.

In some embodiments, as discussed below, the housing is used as a "dumb" medicine holder. In this configuration, a user can snap the housing into a separate module in order to provide command and control functions. A user could upgrade the "dumb" medicine holder to be a "smart" medicine holder capable of carrying out the operations discussed above, such as pairing with a smart phone application, automated locking and unlocking, and data collection such as open and closed times or frequency or time-temperature limits.

The structure of the device can be fabricated from plastics or other structural materials and molding or fabrication processes which will be known to one skilled in the art of manufacturing.

In another non-limiting embodiment of the present invention as shown in FIGS. 5-11, device 200 includes a housing 202 and a drawer 206 being lockable to the housing to form a closed or an open unit. Bottom surface 210 of housing 202 includes an aperture for a removable door 218 for accessing a battery located within the housing. The battery can be used to provide power to the device.

The housing 202 includes an automated locking mechanism 260 to lock the drawer 206 and the housing 202 together until a medication dose is scheduled to be taken. The locking mechanism is operated by a smart phone application 60 using a wireless communication protocol and a smart phone as discussed above. When the pre-determined time set in the application occurs, and the smart phone is in proximity with a wireless electronic communication module 252 which can be located in the housing or the drawer, when the smart phone is "paired", a signal can be sent enabling the lock to open and allow a user access to the medicine via by opening the drawer. A signal from the smart phone will enable a mechanical device such for example, a solenoid, an actuator, or a magnet to open or close the lock. A person of ordinary skill in the electro-mechanical arts will understand that the locking and unlocking function can be carried out in a number of known ways.

The housing can include by-pass switch 240 to allow a user to unlock the lid in case of emergency or malfunction and to allow access to the contents of the housing. The use of the by-pass switch can be electronically recorded and sent to the smart phone application for review and analysis.

The housing 202 and drawer can include a light strip 244, such as, for example an LED light, or an illuminated area which can illuminate, change color, or flash when it is time to take a medication stored inside the housing, when the device malfunctions, when the device is paired to a smart phone, or when the device is low on power.

In this embodiment, housing 202 includes switch 248 for sensing when the drawer is opened or closed. The switch 248 can be, for example, an electrical switch, a mechanical switch, or an optical switch or other sensor.

The housing 202 or drawer 206 can also include a wireless electronic communication module 252 and associated hardware necessary to carry out the wireless command and control function and to communicate information to the smart phone and the application residing on the phone. Information regarding the status of the drawer, including when it is opened and closed, or how many times it opened or closed, can be transmitted to the smart phone and utilized by the application to provide user data.

In this embodiment, temperature sensor 256 can be used to record the temperature of the housing or drawer where medicine resides in order to monitor the condition of the medicine. The sensor 256 can send temperature data via the wireless connection protocol to the smart phone which can be utilized by the application to provide user data about temperature conditions during storage, such as, for example, the minimum and maximum temperatures over time.

In use, as discussed above, a user installs a custom software application 60 on a smart phone (See FIGS. 6-7). After the application "pairs" the smart phone with a wireless chip set or wireless transceiver 252 in the housing or drawer, the lock mechanism 260 can be disengaged and the user can open the drawer.

Next, the user can load injectable medicines 264 or other medicines into the storage areas 268 of the drawer and close the drawer to lock the contents inside the housing and start a dosing regimen.

In this embodiment, the application can be programmed to send the user an alarm on the smart phone or illuminate the light 244 at pre-determined times.

When the user next approaches the device, (i.e. the smart phone and device will remain "paired" and will connect wirelessly when the phone is in range of the housing) the smart phone application can be used to open the locking mechanism by sending a wireless signal to actuate the locking mechanism. The user can now access the medicine 264 stored in the device.

When the user accesses the medicine, the sensors 272 can electronically time stamp each time the drawer is opened or closed. Further, each sensor 272 can be configured to detect the presence or the absence of a medicine 264 within each storage area location 268.

This access data can be sent to the smart phone application for review and analysis. After each use, the drawer is closed and locked. A timer in the application restarted so that when the next dose is due, the process is repeated.

In some embodiments, the housing includes a battery or a rechargeable battery. Optionally, the housing can be powered by an external power source, such as by a plug and power outlet and can include a backup battery.

In one embodiment, the housing or drawer can include a light sensor to determine whether the housing is in a lighted place or in a dark place. If, for example, if the housing is kept in a dark refrigerator, the sensor can signal the device to enter a "sleep mode" thereby saving power and extending the life of the battery. When the refrigerator is opened and ambient light is detected by the sensor, the device will enter a "wake" mode to perform its required functions as discussed above.

In one embodiment, as discussed further below, the housing is used as a "dumb" medicine holder. In this configuration, a user can snap the housing into a separate module in order to provide command and control functions. A user could upgrade the "dumb" medicine holder to be a "smart" medicine holder capable of carrying out the operations discuss above, such as pairing with a smart phone application, automated locking and unlocking, and data collection such as open and closed times or frequency or time-temperature limits.

Once again referring to FIGS. 6A and 6B, the smart phone application 60 includes a scheduling screen 62. When a medicine is due, the use will receive a visual or audible prompt 64. As the user approaches the device 200 with the paired smartphone, the application can display a reminder screen 66 (FIG. 6B) in order to prompt the user to open the drawer 206 or to snooze until a later time when the user wants to take the medicine 264.

Referring to FIGS. 7A-7C, three example screens for application 60 are shown. Screen 72 depicts an adherence chart indicating the overall patient compliance to the medicine schedule. Screen 74 depicts a schedule screen that shows the user which medicines are due, the time and the date due. Screen 76 depicts the history of when the medicine was taken so that a user may review the prior dosing history.

The user interface has a graphical display designed for ease of use. The user is guided through a series of steps to set up and program the device, dispense medications and perform other desirable functions as described.

In another non-limiting embodiment of the present invention as shown in FIGS. 12-16, device 300 includes a housing 302 and a drawer 206 being lockable to the housing to form a closed or an open unit. Bottom surface 310 of housing 302 includes a child safety latch 314 for interlocking with a release mechanism 316 located on drawer 206. The latch can be manually opened by an adult or someone who is familiar with proper use of the device 300.

The housing 302 can be augmented by assembly with smart wireless component (SMC) 310 which includes an automated locking mechanism, such as a solenoid, 360 (See FIG. 16) to lock the drawer and the housing until a medication dose is scheduled to be taken. The locking mechanism is operated by a smart phone application using a wireless communication protocol and a smart phone as discussed above. When the pre-determined time set in the application occurs, and the smart phone is in proximity with the SMC 310, the SMC and the smart phone are "paired", thus enabling the lock to open and allow a user access to the medicine via by opening the drawer. A signal from the smart phone will enable a mechanical device such as an actuator, solenoid, or a magnet to open or close the lock. A person of ordinary skill in the electro-mechanical arts will understand that the locking and unlocking function can be carried out in a number of known ways.

The SMC 310 includes by-pass feature 314. When the SMC is engaged with the housing, the by-pass feature disengages child safety latch 314 such that the locking an unlocking of the drawer and housing is controlled by the SMC locking mechanism 360.

The housing 302 and drawer can include a light strip 344, such as, for example an LED light, or an illuminated area which can illuminate, change color, or flash when it is time to take a medication stored inside the housing, when the device malfunctions, when the device is paired to a smart phone, or when the device is low on power.

In this embodiment, housing 302 includes switch 348 for sensing when the lid is opened or closed. The switch 348 can be, for example, an electrical switch, a mechanical switch, or an optical switch or other sensor. The SMC includes a wireless chip set or wireless electronics module and associated hardware necessary to carry out the wireless command and control function and to communicate information to the smart phone and the application residing on the phone. Information regarding the status of the drawer, including when it is opened and closed, or how many times it opened or closed, can be transmitted to the smart phone and utilized by the application to provide user data.

In this embodiment, temperature sensor 356 can be used to track the temperature of the housing where medicine resides in order to monitor the condition of the medicine. The sensor 356 can send temperature data via the wireless connection protocol to the smart phone which can be utilized by the application to provide user data about temperature conditions during storage, such as, for example, the minimum and maximum temperatures over time.

In use, as discussed above, a user installs a custom software application on a smart phone (See FIGS. 6-7A-7C). After the application "pairs" the smart phone with a wireless chip set or wireless transceiver in the SMC, the lock 360 can be disengaged and the user can open the drawer.

Next, the user can load injectable materials 364 or other medicines into the drawer and close the drawer to lock the contents inside the housing and start a dosing regimen.

In this embodiment, the application can be programmed to send the user an alarm on the smart phone or illuminate the light 344 at pre-determined times.

When the user next approaches the device, (i.e. the smart phone and device will remain "paired" and will connect wirelessly when the phone is in range of the SMC) the smart phone application can be used to open the locking mechanism by sending a wireless signal to actuate the locking mechanism. The user can now access the medicine 364 stored in the device.

When the user accesses the medicine, the sensor 348 can electronically time stamp each time the drawer is opened or closed.

This data can be sent to the smart phone application for review and analysis. After each use, the drawer is closed and locked. A timer in the application restarted so that when the next dose is due, the process is repeated.

In some embodiments, the housing includes a battery or a rechargeable battery. Optionally, the housing can be powered by an external power source, such as by a plug and power outlet and can include a backup battery.

In one embodiment, the housing, drawer or SMC, can include a light sensor to determine whether the housing is in a lighted place or in a dark place. If, for example, if the housing is kept in a dark refrigerator, the sensor can signal the device to enter a "sleep mode" thereby saving power and extending the life of the battery. When the refrigerator is opened and ambient light is detected by the sensor, the device will enter a "wake" mode to perform its required functions as discussed above.

EXAMPLES

In use, a doctor can explain to a patient that self-injection will be necessary to effectively treat the patient's condition. The patient can be instructed on how to self-inject, and how to safely dispose of the used syringe. This instruction can be given by a clinical nurse educator or other health professional.

An injection schedule, specifying dose and frequency can be provided to the patient. Once the injection schedule is determined, the clinical nurse educator or the patient's pharmacist can program an application that resides on a smart phone or other device with the details of the patient's injection schedule.

For example, the patient may be required to self-inject three times each week, on Monday mornings at 10:00 am.

In practice, on Monday morning at 10:00 am each week the smart phone will sound an alarm reminding the patient that a self-injection is scheduled.

Unlike other applications that merely provide alarm reminders, the instant alarm can only be turned off by opening the lid or the drawer of the device, which may be stored in the patient's refrigerator.

If the time is inconvenient for the patient, the patient can interact with a prompt to the question "Do you want to administer your injection now", to "snooze" the alarm.

Once the lid or the drawer is opened, a sensor sends a signal via the wireless antenna to the smart phone application, which in turn can send a message, for example an e-mail or a text message, to the patient's caretaker or health care professional.

After the device is programmed and loaded, the smart phone will alert the user when it is time to take the appropriate medication. First, the smart phone signals the user with a visual or audible alarm or both. The audible alarm can be selected from the audio files residing on the phone. For example, a ring tone or a song may act as an audible alarm. At the same time, the phone screen can display a visual alert including the dose time, an image of the pills to be taken and their names.

To dispense the medication, the smart phone is paired to the wireless electronic located in the device. A signal from the phone unlocks the lid or the drawer of the appropriate compartment. The user can slide the drawer out or open the lid to access the proper medicine at the proper time.

The phone will enter an alert mode when a dose is missed. The phone screen will display which medications were missed along with the dose time and images of the missed medications. Further, the application can provide useful instructions to the user regarding what to do in the event of a missed dose and provides instant access to the prescribing doctor's phone number. With a single touch of the phone touch screen, the patient can call the prescribing doctor for additional advice. The smart phone can also provide internet hyperlinks to the medicine manufacturer's website for additional information about each medication.

When the lid is opened or the drawer is accessed, a signal can be sent from the phone via a wireless network to a user's private database. The database can be maintained on the phone and on a secure server. The database can be synchronized. The network can be a cell phone network, a Wi-Fi network or any other type of wireless network.

In one embodiment, the application may include the ability to communicate through a hard line network such as a cable network or fiber optics network to connect to the internet.

Dispensing data can be communicated to a remote server database; the data is available for review by the user or a care taker. The data may be presented in any number of ways including charts, graphs or tables. In this way, the user's medication dispensing history can be reviewed for compliance with the desired schedule for taking medications.

In one embodiment, the application includes a feature which alerts a care taker that a dose has not been dispensed via a wireless network. For example, application generates a phone message, text message or e-mail message which is sent directly to the user, care taker, doctor or any number of interested parties. This feature can be particularly useful when, for example, a care taker or family member desires to monitor the medication dispensing compliance of a senior citizen such as a parent or family member or individual who may be suffering from a memory disorder or who may simply be forgetful. When the user receives a "missed dose" message, appropriate action can be taken in real-time to correct the short term non-compliance and address the longer term issues associated with the inability or unwillingness of a patient to comply with a medication schedule. This process is described in more detail below.

As illustrated above, users can input data for numerous medications into the smart phone application. Medication specific supplementary information can also be provided directly by the manufacturer for one or more medications. Supplementary information can include, for example, the name of the medication, its function, how and when the medication should be taken, missed dose information, information about side effects including specific actions required if the patient experiences side effects, possible interactions with other medications, and where the patient can find additional information about the medication, such as hyperlinks to the manufacturer's website. Further, manufacturers can send coupons and other desirable information such as, for example, safety alerts directly to users through the wireless network.

The smart phone includes a software application that is programmed to store a medicine and schedule data for one or more medications. The phone database stores medicine and schedule information that is input by the user or acquired from the manufacture's database. The phone database can be used to command the locking lid or drawer locks to locked or unlocked positions. When a dose is dispensed or missed by the user, the phone communicates with the secure server database. The server database can be accessed by users having a password and a username. Authorized users can login to the database to monitor patient compliance.

It is contemplated that numerous graphs and reports can be displayed or printed such that the person accessing the database can easily recognize compliance problems, determine whether there are any recurring compliance problems, or print medication lists.

As previously described, the database can communicate with a monitoring module. In the event of a compliance problem, for example, a missed dose of heart medication, the module can issue commands to send an alarm or alarms to concerned individuals by e-mail, text or other means. In this way, a care taker can be timely notified of a missed dose and can implement corrective action.

As will also be appreciated, a significant benefit of the present invention includes the ability to store the user's medicine schedule on a smart phone which the user may carry with them. A patient's medication information can be invaluable to a new doctor or in the event a user is taken to the hospital. The present invention allows a nurse, doctor, EMT or other health care professional to access a patient's medication regimen or dispensing history by accessing a smart phone or a server database. This feature can dramatically reduce the risk of prescribing the wrong medication and also reduce the time before necessary treatment is administered.

Further, the patient can be directed by the application to gather the other items necessary for self-injection. These items can include, but are not limited to, alcohol swabs to clean the injection site and adhesive bandages to cover the site after the injection. While the patient gathers the necessary supplies the smart phone can display, for example, the last five injection sites that the patient has used. This information can be utilized by the patient to pick the best site for the next injection. Once the patient completes the injection, she can indicate and record the site chosen by touching a body diagram on a smart phone application screen.

If the patient is confused about any aspect of the self-injection process, a virtual button on the smart phone can offer the patient an opportunity to review a video that provides instructions for each step of self-injection process. At any time, when the wireless or bluetooth antenna is paired with the smart phone, whether the housing is opened or not, the application can display the temperature history or the minimum and maximum temperatures for a selected period of time. This information can be important because certain expensive pharmaceuticals cannot be used if they have been frozen or if they have become too warm.

After an injection has been completed, the smart phone can prompt the patient to properly dispose of the used syringe in a proper disposal or sharps container. The patient can confirm the completion of the self-injection process on the smart phone.

The device can be changed and reconfigured and still achieve the desired goal, for example the sensor that records the opening and closing of the storage box could instead be substituted with a sensor on a sharps container that records when a syringe is disposed.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus for improving patient compliance, comprising:
   (a) a housing, said housing having an attached rotatable hinged lid and a lock for locking or unlocking said lid;
   (b) a first sensor, said sensor to detect a position of said lid, said sensor being attached to said housing;
   (c) a second sensor, said second sensor attached within said housing to detect a presence or an absence of an injectable medication;
   (d) a wireless transceiver for transmitting said position of said lid to a smart device application, said wireless transceiver being attached to said housing, wherein said wireless transceiver communicates a signal to a user database, said signal indicating at least one time when said lid has been opened, and wherein said user database stores a data set indicating whether or not said lid has been opened thereby allowing a user to monitor a compliance with a schedule for taking said injectable medication;
   (e) a smart device, said smart device being capable of wirelessly commanding said lock to an open position or a closed position, wherein said smart device runs said smart device application for determining a pre-determined time for reminding a user to unlock said lid based on a medication data set input by said user and for receiving and recording said position of said lid;
   (f) a manual bypass switch for unlocking said lid in an emergency;
   (g) a light for signaling said user that said lid is unlocked;
   h) a light sensor for detecting when said apparatus is stored in a dark condition and a light condition, thereby commanding said apparatus to enter a sleep mode for saving power when said apparatus is in said dark condition and to enter an awake mode for operation when said apparatus is in said light condition;
   (i) a temperature sensor to detect and transmit a temperature of said housing to said smart device application for determining a temperature history of said injectable medication stored within said housing; and (j) said smart device transmitting a lock data set to a secure server database, said lock data set including confirmation of times when said housing was unlocked and locked.

2. A method of improving patient compliance with a pre-determined medication schedule comprising:

(a) entering a medication data set into a smart device application residing on a smart device, said medication data set including a name of one of more medication, a strength of said one or more medication, and a time that said one or more medication is to be taken;

(b) loading one or more injectable medications into a lockable housing, said housing including a rotatably hinged lockable lid;

(c) receiving an audible or visual alarm from said smart device application residing on said smart device;

(d) using a wireless protocol generated by said smart device to unlock or to lock said housing lid to access said one or more injectable medications;

(e) transmitting a lock data set from said smart device to a secure server database, said lock data set including confirmation of times when said housing was unlocked and locked;

(f) transmitting a temperature data set from said smart device to a secure server database, said temperature data set including a minimum or a maximum temperature of said one or more injectable medications;

(g) transmitting an alarm from said smart device when said lockable housing is not unlocked within a predetermined time from a scheduled medication dispensing time;

(h) transmitting an alarm from said smart device when said minimum or maximum temperature is not within a predetermined temperature range;

(i) transmitting a signal from a sensor to said smart device, said signal indicating a presence or an absence of said one or more injectable medications in said housing; and (j) detecting when said apparatus is stored in a dark condition and in a light condition, thereby commanding said apparatus to enter a sleep mode for saving power when said apparatus is in said dark condition and to enter an awake mode for operation when said apparatus is in said light condition.

3. An apparatus for improving patient compliance comprising:

(a) a housing, said housing including a bottom portion and a rotatable hinged lid, said bottom portion including a removable door for accessing a battery;

(b) a light, said light being disposed within said housing, wherein said light can illuminate, change color, or flash at a predetermined medication time, thereby indicating to a user said time to use an injectable medication stored within said housing, or indicating when said apparatus malfunctions, or indicating when said apparatus is paired to a smart phone, or indicating when said battery's power is low;

(c) a lid position switch, said switch being mounted between said housing and said lid, said switch for determining a time when said lid is opened or closed;

(d) a bypass switch, said switch being mounted to said housing for allowing a user to manually unlock said lid to allow access to an injectable medication stored in said housing in case of emergency or malfunction and to record and send a bypass switch history data set to a smart phone application for review and analysis by said user;

(e) an automatic locking mechanism, said mechanism being operated by said smart phone application using a wireless communication protocol and a smart device, wherein when a pre-determined time set in said smart phone application occurs and said smart device is in wireless proximity with a wireless transceiver in said housing, the housing and the smart device are paired, thereby enabling said automatic locking mechanism to open and allowing said user to access said injectable medication;

(f) said smart device transmitting a lock data set to a secure server database, said lock data set including confirmation of times when said housing was unlocked and locked; and (g) a light sensor for detecting when said apparatus is stored in a dark condition and in a light condition, thereby commanding said apparatus to enter a sleep mode for saving power when said apparatus is in said dark condition and to enter an awake mode for operation when said apparatus is in said light condition.

4. The apparatus of claim 3, further including: (h) a temperature sensor to detect and transmit a temperature of said housing to said smart device application for determining a temperature history of said injectable medication stored within said housing.

5. The apparatus of claim 3, further including: (i) a position sensor, said sensor being mounted within said housing, said sensor being configured to determine a presence or an absence of an injectable medication within said housing and to send a position data signal via said wireless connection protocol to said smart device application thereby providing said user a use history of said injectable medication.

* * * * *